United States Patent
Weckwerth et al.

(10) Patent No.: US 7,413,567 B2
(45) Date of Patent: Aug. 19, 2008

(54) OPTICAL SENSOR AND METHOD FOR IDENTIFYING THE PRESENCE OF SKIN

(75) Inventors: Mark V. Weckwerth, Pleasanton, CA (US); Tobin C. Island, Oakland, CA (US); Robert E. Grove, Pleasanton, CA (US)

(73) Assignee: SpectraGenics, Inc., Pleasanton, CA (US)

( * ) Notice: Subject to any disclaimer, the term of this patent is extended or adjusted under 35 U.S.C. 154(b) by 650 days.

(21) Appl. No.: 10/787,720

(22) Filed: Feb. 25, 2004

(65) Prior Publication Data
US 2004/0167502 A1 Aug. 26, 2004

Related U.S. Application Data

(60) Provisional application No. 60/450,243, filed on Feb. 25, 2003, provisional application No. 60/450,598, filed on Feb. 26, 2003, provisional application No. 60/451,091, filed on Feb. 28, 2003, provisional application No. 60/452,304, filed on Mar. 4, 2003, provisional application No. 60/451,981, filed on Mar. 4, 2003, provisional application No. 60/452,591, filed on Mar. 6, 2003, provisional application No. 60/456,379, filed on Mar. 20, 2003, provisional application No. 60/456,586, filed on Mar. 21, 2003, provisional application No. 60/458,861, filed on Mar. 27, 2003, provisional application No. 60/472,056, filed on May 20, 2003.

(51) Int. Cl.
*A61B 18/18* (2006.01)

(52) U.S. Cl. .............................. 606/10; 606/9; 606/12; 607/88

(58) Field of Classification Search ............... 606/3–12; 607/88–91; 128/898
See application file for complete search history.

(56) References Cited

U.S. PATENT DOCUMENTS

| 3,307,533 A | 3/1967 | Liebner |
| 3,538,919 A | 11/1970 | Meyer |
| 3,622,743 A | 11/1971 | Muncheryan |

(Continued)

FOREIGN PATENT DOCUMENTS

CN 2442726 U 8/2001

(Continued)

OTHER PUBLICATIONS

U.S. Appl. No. 10/794,676, filed Mar. 3, 2004, Weckworth et al.

(Continued)

*Primary Examiner*—Ahmed M Farah
(74) *Attorney, Agent, or Firm*—James E. Eakin

(57) ABSTRACT

A sensor for detecting the presence of skin is disclosed, one configuration of which uses multiple light emitting diodes, each of a unique wavelength band, and a broad-band photodetector to measure the remission of light at multiple wavelengths from a material being analyzed. Characteristics of the spectral remission of the material are used to discriminate human skin from materials that are not human skin. Further, an aesthetic medical device utilizing such a sensor in which the device is inhibited from operation if skin has not been detected. The incorporation of a skin sensor improves the safety of devices that emit radiation that otherwise would pose a hazard if not directed onto skin.

34 Claims, 6 Drawing Sheets

U.S. PATENT DOCUMENTS

| | | | |
|---|---|---|---|
| 3,693,623 A | 9/1972 | Harte | |
| 3,821,510 A | 6/1974 | Muncheryan | |
| 3,834,391 A | 9/1974 | Block | |
| 4,232,678 A | 11/1980 | Skovasjsa | |
| 4,354,092 A | 10/1982 | Manabe et al. | |
| 4,388,924 A | 6/1983 | Weismann | |
| 4,423,736 A | 1/1984 | DeWitt et al. | |
| 4,551,628 A | 11/1985 | Grossman | |
| 4,573,466 A | 3/1986 | Simada et al. | |
| 4,592,353 A | 6/1986 | Daikuzono | |
| 4,608,978 A | 9/1986 | Rohr | |
| 4,617,926 A | 10/1986 | Sutton | |
| 4,690,141 A | 9/1987 | Castel | |
| 4,733,660 A | 3/1988 | Itzkan | |
| 4,829,262 A | 5/1989 | Furumoto | |
| 4,846,184 A | 7/1989 | Comment et al. | |
| 4,905,690 A | 3/1990 | Ohshiro et al. | |
| 4,930,504 A | 6/1990 | Diamantopoulos et al. | |
| 5,057,104 A | 10/1991 | Chess | |
| 5,059,013 A | 10/1991 | Jain | |
| 5,059,192 A | 10/1991 | Zaias | |
| 5,071,417 A * | 12/1991 | Sinofsky | 606/8 |
| 5,075,971 A | 12/1991 | McCambridge | |
| 5,109,465 A | 4/1992 | Klopotek | |
| 5,226,907 A | 7/1993 | Tankovich | |
| 5,259,380 A | 11/1993 | Mendes et al. | |
| 5,282,797 A | 2/1994 | Chess | |
| 5,344,418 A | 9/1994 | Ghaffari | |
| 5,360,426 A | 11/1994 | Muller et al. | |
| 5,401,270 A | 3/1995 | Mueller | |
| 5,405,368 A | 4/1995 | Eckhouse | |
| 5,425,728 A | 6/1995 | Tankovich | |
| 5,431,647 A | 7/1995 | Purcell, Jr. | |
| 5,464,434 A | 11/1995 | Alt | |
| 5,464,436 A | 11/1995 | Smith | |
| 5,473,408 A | 12/1995 | Hoffman et al. | |
| 5,486,172 A | 1/1996 | Chess | |
| 5,519,534 A | 5/1996 | Smith | |
| 5,549,660 A | 8/1996 | Mendes et al. | |
| 5,556,612 A | 9/1996 | Anderson | |
| 5,595,568 A | 1/1997 | Anderson et al. | |
| 5,606,798 A | 3/1997 | Kelman | |
| 5,624,435 A | 4/1997 | Furumoto | |
| 5,628,744 A | 5/1997 | Coleman et al. | |
| 5,630,811 A | 5/1997 | Miller | |
| 5,632,741 A | 5/1997 | Zavislan | |
| 5,643,252 A | 7/1997 | Waner et al. | |
| 5,647,866 A | 7/1997 | Zaias | |
| 5,658,323 A | 8/1997 | Miller | |
| 5,662,643 A * | 9/1997 | Kung et al. | 606/3 |
| 5,669,916 A | 9/1997 | Anderson | |
| 5,683,380 A | 11/1997 | Eckhouse | |
| 5,700,240 A | 12/1997 | Barwick, Jr. | |
| 5,707,403 A | 1/1998 | Grove et al. | |
| 5,728,090 A | 3/1998 | Martin | |
| 5,735,844 A | 4/1998 | Anderson et al. | |
| 5,743,901 A | 4/1998 | Grove | |
| 5,752,948 A | 5/1998 | Tankovich | |
| 5,752,949 A | 5/1998 | Tankovich | |
| 5,766,214 A | 6/1998 | Mehl, Sr. | |
| 5,769,844 A | 6/1998 | Ghaffari | |
| 5,817,089 A | 10/1998 | Tankovich | |
| 5,820,625 A | 10/1998 | Izawa | |
| 5,824,023 A | 10/1998 | Anderson | |
| 5,843,072 A | 12/1998 | Furumoto | |
| 5,846,252 A | 12/1998 | Mehl, Sr. | |
| 5,849,029 A | 12/1998 | Eckhouse | |
| 5,853,407 A | 12/1998 | Miller | |
| 5,868,732 A | 2/1999 | Waldman | |
| 5,871,479 A | 2/1999 | Furumoto | |
| 5,871,480 A | 2/1999 | Tankovich | |
| 5,871,521 A | 2/1999 | Kaneda | |
| 5,879,346 A | 3/1999 | Waldman | |
| 5,885,273 A | 3/1999 | Eckhouse | |
| 5,966,210 A | 10/1999 | Roscow et al. | |
| 5,968,034 A | 10/1999 | Fullmer et al. | |
| 5,989,267 A | 11/1999 | Anderson | |
| 6,015,404 A * | 1/2000 | Altshuler et al. | 606/9 |
| RE36,634 E | 3/2000 | Ghaffari | |
| 6,059,765 A | 5/2000 | Cole | |
| 6,080,146 A | 6/2000 | Altshuler | |
| 6,096,029 A | 8/2000 | O'Donnell, Jr. | |
| 6,104,959 A * | 8/2000 | Spertell | 607/101 |
| 6,106,514 A | 8/2000 | O'Donnell, Jr. | |
| 6,138,041 A | 10/2000 | Yahia | |
| 6,160,831 A | 12/2000 | Kleinschmidt | |
| 6,183,500 B1 | 2/2001 | Kohler | |
| 6,183,773 B1 | 2/2001 | Anderson | |
| 6,188,495 B1 | 2/2001 | Inoue | |
| 6,197,020 B1 | 3/2001 | O'Donnell, Jr. | |
| 6,208,749 B1 | 3/2001 | Gutkowicz-Krusin et al. | |
| 6,214,034 B1 * | 4/2001 | Azar | 607/89 |
| 6,228,074 B1 | 5/2001 | Almeida | |
| 6,251,127 B1 | 6/2001 | Biel | |
| 6,269,818 B1 | 8/2001 | Lui et al. | |
| 6,273,884 B1 | 8/2001 | Altshuler | |
| 6,273,885 B1 | 8/2001 | Koop et al. | |
| 6,277,111 B1 | 8/2001 | Clement | |
| 6,280,438 B1 | 8/2001 | Eckhouse | |
| 6,290,713 B1 | 9/2001 | Russell | |
| 6,379,376 B1 | 4/2002 | Lubart | |
| 6,436,127 B1 | 8/2002 | Anderson et al. | |
| 6,440,122 B1 | 8/2002 | Shimoji | |
| 6,441,943 B1 | 8/2002 | Roberts | |
| 6,494,900 B1 | 12/2002 | Salansky et al. | |
| 6,508,813 B1 * | 1/2003 | Altshuler | 606/9 |
| 6,511,475 B1 | 1/2003 | Altshuler | |
| 6,514,242 B1 | 2/2003 | Vasily | |
| 6,516,013 B1 | 2/2003 | Patzel | |
| 6,517,532 B1 | 2/2003 | Altshuler | |
| 6,533,775 B1 | 3/2003 | Rizoiu | |
| 6,548,781 B1 | 4/2003 | Brunwinkel | |
| 6,563,853 B2 | 5/2003 | Heist | |
| 6,600,951 B1 | 7/2003 | Anderson | |
| 6,605,080 B1 | 8/2003 | Altshuler | |
| 6,610,052 B2 | 8/2003 | Furumoto | |
| 6,641,044 B2 | 11/2003 | Plesko | |
| 6,648,904 B2 | 11/2003 | Altshuler | |
| 6,653,618 B2 | 11/2003 | Zenzie | |
| 6,659,999 B1 | 12/2003 | Anderson et al. | |
| 6,660,000 B2 | 12/2003 | Neuberger et al. | |
| 6,663,620 B2 | 12/2003 | Altshuler | |
| 6,663,659 B2 | 12/2003 | McDaniel | |
| 6,666,856 B2 | 12/2003 | Connors et al. | |
| 6,723,090 B2 | 4/2004 | Altshuler et al. | |
| 6,902,563 B2 | 6/2005 | Wilkens et al. | |
| 6,955,672 B2 * | 10/2005 | Cense et al. | 606/9 |
| 7,029,469 B2 * | 4/2006 | Vasily | 606/9 |
| 2001/0023363 A1 | 9/2001 | Harth et al. | |
| 2002/0005475 A1 | 1/2002 | Zenzie | |
| 2002/0015430 A1 | 2/2002 | Osmanow | |
| 2002/0031160 A1 | 3/2002 | Desor | |
| 2002/0049483 A1 | 4/2002 | Knowlton | |
| 2002/0091377 A1 | 7/2002 | Anderson | |
| 2002/0097587 A1 | 7/2002 | Krietzman | |
| 2002/0128635 A1 | 9/2002 | Altshuler | |
| 2002/0128695 A1 | 9/2002 | Harth et al. | |
| 2002/0151887 A1 | 10/2002 | Stern et al. | |
| 2002/0161357 A1 | 10/2002 | Anderson et al. | |
| 2002/0161418 A1 | 10/2002 | Wilkens et al. | |
| 2002/0173780 A1 | 11/2002 | Altshuler | |
| 2002/0173833 A1 | 11/2002 | Korman et al. | |
| 2002/0183811 A1 | 12/2002 | Irwin | |
| 2003/0004499 A1 | 1/2003 | McDaniel | |

| | | | |
|---|---|---|---|
| 2003/0009158 A1 | 1/2003 | Perricone | |
| 2003/0032950 A1 | 2/2003 | Altshuler | |
| 2003/0036751 A1 | 2/2003 | Anderson | |
| 2003/0046825 A1 | 3/2003 | Slingo | |
| 2003/0050561 A1 | 3/2003 | Bazin et al. | |
| 2003/0055413 A1 | 3/2003 | Altshuler | |
| 2003/0055414 A1 | 3/2003 | Altshuler | |
| 2003/0065314 A1 | 4/2003 | Altshuler | |
| 2003/0094714 A1 | 5/2003 | Buazza et al. | |
| 2003/0105069 A1 | 6/2003 | Robinson et al. | |
| 2003/0133292 A1 | 7/2003 | Mueller et al. | |
| 2003/0138249 A1 | 7/2003 | Merloa et al. | |
| 2003/0146122 A1 | 8/2003 | Westfield et al. | |
| 2003/0169400 A1 | 9/2003 | Buazza et al. | |
| 2003/0177657 A1 | 9/2003 | Andis | |
| 2003/0195494 A1 | 10/2003 | Altshuler et al. | |
| 2003/0199859 A1 | 10/2003 | Altshuler et al. | |
| 2003/0216795 A1 | 11/2003 | Harth et al. | |
| 2003/0233138 A1 | 12/2003 | Spooner | |
| 2004/0006328 A1 | 1/2004 | Anderson | |
| 2004/0010298 A1 | 1/2004 | Altshuler | |
| 2004/0010299 A1 | 1/2004 | Tolkoff | |
| 2004/0034319 A1 | 2/2004 | Anderson et al. | |
| 2004/0034341 A1 | 2/2004 | Altshuler et al. | |
| 2004/0036975 A1 | 2/2004 | Slatkine | |
| 2004/0073079 A1 | 4/2004 | Altshuler et al. | |
| 2004/0093042 A1 | 5/2004 | Altshuler et al. | |
| 2004/0122492 A1 | 6/2004 | Harth et al. | |
| 2004/0167499 A1 | 8/2004 | Grove | |
| 2004/0167500 A1 | 8/2004 | Weckworth et al. | |
| 2004/0167501 A1 | 8/2004 | Island | |
| 2004/0167592 A1 | 8/2004 | Grove et al. | |
| 2004/0176754 A1* | 9/2004 | Island et al. | 606/9 |
| 2004/0176823 A1 | 9/2004 | Island et al. | |
| 2004/0225339 A1* | 11/2004 | Yaroslavsky et al. | 607/88 |

FOREIGN PATENT DOCUMENTS

| | | |
|---|---|---|
| DE | 196 29 978 A1 | 1/1998 |
| EP | 0 933 096 A2 | 8/1999 |
| EP | 1 116 476 A2 | 7/2001 |
| EP | 1 168 535 A1 | 1/2002 |
| EP | 0 761 257 A2 | 3/2003 |
| FR | 2 665 366 | 2/1992 |
| JP | 11-244295 | 9/1999 |
| JP | 2000-300683 | 10/2000 |
| WO | WO 00-02491 | 1/2000 |
| WO | WO 02-094116 A1 | 11/2002 |
| WO | WO 03-017824 A2 | 3/2003 |
| WO | WO 03-049633 A1 | 6/2003 |

OTHER PUBLICATIONS

Sliney, David, et al., "Safety With Lasers And Other Optical Sources, A Comprehensive Handbook", Plenum Press (1985), pp. 223-224, 477-480.
Hode, L., "Are Lasers More Dangerous Than IPL Instruments?", Lasers In Surgery And Medicine, Supplement, 15, 2003, p. 6; and poster presentation at corresponding conference.
2002 Skin & Aging, Supplement to Nov. 2002, "Harnessing Light to Treat Stretch Marks and Other Hypopigmented Scars", pp. 1-4.
Predicate Devices: LightSheer Diode Laser System by Star in 1997, K973324, K982940, K001746.
Predicate Devices: SLP 1000 (LC 100) Diode Laser of Palomar Medical Technologies, K010580, K011747.
Predicate Devices: Apex 800 Pulsed Diode Laser of IRIDEX Corporation, K020849.
Predicate Devices: F1 Pulsed Diode Laser of Opus Medical, Inc., K030235.
IEC Technical Report 60825-8, Safety of Laser Products—Guide for the Safe Use of Medical Laser Equipment.
International Standard IEC 60825.1, Safety of Laser Products—Part 1: Equipment Classification, Requirements and User's Guide, Edition 1.2, Aug. 2001, p. 11; p. 40, Note 2, Sub-note D; p. 52; p. 79.
Predicate Devices: LightSheer Diode Laser System manufactured by Lumenis, Ltd.
Predicate Devices: Quantum Flash Lamp System manufactured by Lumenis, Ltd.
Predicate Devices: CoolGlide Excel YAG Laser by Altus, Inc.
Predicate Devices: Devices by Ya-Man, Ltd., of Tokyo, Japan.
Class I Laser Device under the Guidelines of the U.S. Food and Drug Administration Center for Devices and Radiological Health, 2 pages.
Predicate Devices: Oriel Instruments Model 48010, by Spectra-Physics, Stratford, CT.
Predicate Devices: Panasonic part No. P-170SCW, or HHR300SCP Ni-MH Rechargables, Panasonic P-170SCRP NiCd, by Panansonic Matsushita Electric Corporation of America, Secaucus, NJ.
Predicate Devices: Laser Diode Bar Packages, part No. ASM06C040W080810B80, Cutting Edge Optronics, of St. Charles, MO.
Predicate Devices: Part No. HX8-101 or FAN-101, or CP 0.8-31-06L, from Melcor.
Predicate Devices: PIC18LF452, manufactured by Microchip Technologies of Chandler, AZ.
Predicate Devices: Transistors IRL3716 (International Rectifier Corp., El Segundo, CA).
Brown, Earle, Modern Optics, Reinhold Publishing Corporation, 1065, p. 225.
Micro Touch Trimmer website, www.assenontvwork.com/vcc/ideavillage/microtouch/104917, printed Dec. 4, 2003, 21 pages.
Palomar Super Long Pulse Diode Laser System, Clinical Data, Palomar medical Technologies brochure.
Morys et al., "The Accurate Measurements Of Biologically Effective Ultraviolet Radiation", Jul. 1993, 10 pages.
UV Index definition, Canadian Environmental Web page, Jun. 1, 1996, See entire document, 3 pages.
Guideline for Limits of Exposure to Ultraviolet Radiation of Wavelengths between 180 nm and 400 nm, Health Physics, vol. 49, No. 2, Aug. 1985, pp. 331-340.
Kjeldstad B, et al., "Porphyrin photosensitization of bacteria," Adv Exp Med Biol. 1985;193:155-9. PMID: 4096295 [PubMed—indexed for Medline], 6 pages.
Arakane K, et al., "Singlet oxygen (1 delta g) generation from coproporphyrin in Propionibacterium acnes on irradiation," Biochem Biophys Res Commun. Jun. 25, 1996;223(3):578-82. PMID: 8687438 [PubMed—indexed for Medline], 5 pgs.
Ashkenazi H, et al., "Eradication of Propionibacterium acnes by its endogenic porphyrins after illumination with high intensity blue light." FEMS Immunol Med Microbiol. Jan 21, 2003;35(1):17-24. PMID: 12589953 [PubMed—indexed for Medline], 8 pgs.
Cornelius CE 3rd, et al., "Red fluorescence of comedones: production of porphyrins by Corynebacterium acnes," J Invest Dermatol. Oct. 1967;49(4):368-70. PMID: 4228644 [PubMed—indexed for Medline], 3 pgs.
Fanta D, et al., "Porphyrinsynthesis of Propionibacterium acnes in acne and seborrhea (author's transl)," Arch Dermatol Res. Apr. 7, 1978;261(2):175-9. German. PMID: 148872 [PubMed—indexed for Medline], 5 pgs.
Formanek I, et al., "[Porphyrinsynthesis by propionibacterium acnes (author's transl)]," Arch Dermatol Res. Aug. 22, 1977;259(2):169-76. German. PMID: 334087 [PubMed—indexed for Medline], 8 pgs.
Kawada A, et al., "Acne phototherapy with a high-intensity, enhanced, narrow-band, blue light source: an open study and in vitro investigation," J Dermatol Sci. Nov. 2002;30(2):129-35. PMID: 12413768 [PubMed—indexed for Medline], 7 pgs.
Kjeldstad B, et al., "An action spectrum for blue and near ultraviolet inactivation of Propionibacterium acnes; with emphasis on a possible porphyrin photosensitization," Photochem Photobiol. Jan. 1986;43(1):67-70. PMID: 3952162 [PubMed—indexed for Medline], 4 pgs.
Kjeldstad B, et al., "Influence of pH on porphyrin production in Propionibacterium acnes," Arch Dermatol Res. 1984;276(6):396-400. PMID: 6517611 [PubMed—indexed for Medline], 5 pgs.
Lee WL, et al., "Comparative studies of porphyrin production in Propionibacterium acnes and Propionibacterium granulosum," J Bacteriol. Feb. 1978;133(2):811-5. PMID: 637914 [PubMed—indexed for Medline], 5 pgs.

McGinley KJ, et al., "Facial follicular porphyrin fluorescence: correlation with age and density of Propionibacterium acnes," Br J Dermatol. Apr. 1980;102(4):437-41. PMID: 7387886 [PubMed—indexed for Medline], 5 pgs.

Meffert H, et al., "Therapy of acne with visible light. Decreased irradiation time by using a blue-light high-energy lamp [transl.]," Dermatol Monatsschr. 1990;176(10):597-603. German. PMID: 21050382 [PubMed—indexed for Medline], 7 pgs.

Meffert H, et al., "Phototherapy of acne vulgaris with the "TuR" UV 10 body section irradiation unit [transl.]," Dermatol Monatsschr. 1986;172(1):9-13. German. PMID: 2938991 [PubMed—indexed for Medline], 6 pgs.

Meffert H, et al., "Phototherapy of acne vulgaris with the UVA irradiation instrument TBG 400[transl.]," Dermantol Monatsschr. 1986;172(2):105-6. German. PMID: 2937663 [PubMed—indexed for Medline], 2 pgs.

Meffert H, et al., "Treatment of acne vulgaris with visible light," Dermatol Monatsschr. 1987;173(11):678-9. German. PMID: 2963772 [PubMed—indexed for Medline], 2 pgs.

Kjeldstad B, et al., "Near-UV-induced radicals in Propionibacterium acnes, studied by electron spin resonance spectrometry at 77 K.," J Photochem Photobiol B. May 1991; 9(2):181-7. PMID: 1650821 [PubMed—indexed for Medline], 7 pgs.

Johnsson A, et al., "Fluorescence from pilosebaceous follicles," Arch Dermatol Res. 1987;279(3):190-3. PMID: 3592747 [PubMed—indexed for Medline], 4 pgs.

Melo TB, et al., "Photodestruction of Propionibacterium acnes porphyrins," Z Naturforsch [C]. Jan.-Feb. 1985 ;40(1-2):125-8. PMID: 3993179 [PubMed—indexed for Medline], 4 pgs.

Melo TB, et al., "In vivo porphyrin fluorescence for Propionibacterium acnes. A characterization of the fluorescing pigments," Dermatologica. Mar. 1982;164(3):167-74. PMID: 7084539 [PubMed—indexed for Medline], 8 pgs.

Mills OH, et al., "Ultraviolet phototherapy and photochemotherapy of acne vulgaris," Arch Dermatol. Feb. 1978;114(2):221-3. PMID: 147054 [PubMed—indexed for Medline], 3 pgs.

Papageorgiou P, et al., "Phototherapy with blue (415 nm) and red (660 nm) light in the treatment of acne vulgaris," Br J Dermatol. May 2000;142(5):973-8. PMID: 10809858 [PubMed—indexed for Medline], 6 pgs.

Romiti R, et al., "High-performance liquid chromatography analysis of porphyrins in Propionibacterium acnes," Arch Dermatol Res. Jun. 2000;292(6):320-2. PMID: 10929774 [PubMed—indexed for Medline], 3 pgs.

Sigurdsson V, et al., "Phototherapy of acne vulgaris with visible light," Dermatology. 1997;194(3):256-60. PMID: 9187844 [PubMed—indexed for Medline], 5 pgs.

Webster, GF, "Inflammation in acne vulgaris," J Am Acad Dermatol. Aug. 1995;33(2 Pt 1):247-53. Review. PMID: 7622652 [PubMed—indexed for Medline], 7 pgs.

Fanta D, et al., "Porphyrin synthesis by propionibacteria in dependence of external factors." Arch Dermatol Res (1981) 271:127-133, 7 pgs.

Leyden J, "Therapy for acne vulgaris," New England Journal of Medicine, Apr. 17, 1997, Review Article, 6 pgs.

Shalita A, et al., "Acne photoclearing (APC) using a novel, high-intensity, enhanced, narrow-band, blue light source," Clinical application notes vol. 9 No. 1, ESC Medical Systems Ltd (Yokneam, Israel) PB 558-0230 Rev. A, 4 pgs.

Shnitkind E, et al., "Anti-inflammatory properties of narrow band blue light," Poster presentation (conference unknown), 1 pg.

Leung, S, "The Porphyrin Page" website at http:--www.washburn.edu-cas-chemistry-sleung-porphyrin-porphyrin_page.html, Created Apr. 16, 1996, Last Modified Nov. 11, 2002, printed Jun. 22, 2004, 7 pgs.

Brunsting, L.A. et al., "The Color of the Skin as Analyzed by Spectrophotometric Methods: III. The Role of Superficial Blood", The Journal of Clinical Investigation, 1929, vol. 7, pp. 593-613.

Brunsting, L. A. et al., "The Color of the Skin as Analyzed by Spectrophotometric Methods: II. The Role of Pigmentation", The Journal of Clinical Investigation, 1929, vol. 7, pp. 574-592.

Angelopoulou et al., "The Reflectance Spectrum of Human Skin", Technical Report, Department of Computer and Information Science, 1999, pp. 1-14.

Parrish, J. et al., Photochemistry and Photobiology, vol. 36, p. 188, Erthema And Melanogenesis Action Spectra Of Normal Human Skin, Solar Light Co., Philadelphia, PA, pp. 187-191.

* cited by examiner

OPTICAL SENSOR AND METHOD FOR IDENTIFYING THE PRESENCE OF SKIN

PRIORITY

This application claims the benefit of priority under 35 U.S.C. § 119(e) to U.S. provisional patent application Nos. 60/450,243, filed Feb. 25, 2003; 60/450,598, filed Feb. 26, 2003; 60/451,091, filed Feb. 28, 2003; 60/452,304, filed Mar. 4, 2003; 60/451,981, filed Mar. 4, 2003; 60/452,591, filed Mar. 6, 2003; 60/456,379, filed Mar. 20, 2003; 60/456,586, filed Mar. 21, 2003; 60/458,861, filed Mar. 27, 2003; and 60/472,056, filed May 20, 2003.

FIELD OF THE INVENTION

This invention relates generally to dermatological diagnostic devices and to dermatological therapeutic devices, and more particularly to dermatological devices that use radiation to probe and treat skin.

BACKGROUND ART

Over the past 15 years, lasers and intense pulsed light systems have been used to treat a wide array of dermatological skin conditions. Examples of such systems are the CoolGlide system manufactured by Altus, Inc. for the treatment of unwanted hair, the Quantum system, manufactured by Lumenis, Inc. for photo rejuvenation, and the VBeam system manufactured by Candela, Inc. for the treatment of vascular lesions. The light emitted by each of these systems is very intense and poses a hazard to both the operator and patient. Undesired or unexpected emission from these systems can cause blindness, skin damage (when cooling mechanisms are not properly applied prior to emission), and damage to furniture, clothing, or other unintended targets. The sale of each of these systems is restricted by the United States Food and Drug Administration (FDA), and the safety of treatments performed by these machines relies on a well-trained operator to determine if conditions are satisfactory for emission. However, even in the hands of a well-trained operator, the safe use of these types of systems would be enhanced if emission from the system were inhibited unless skin was the target.

In the future, devices similar to the above products may be developed that are intended for use by untrained users and offered for sale directly to consumers. Not only will such products benefit from the integration of a sensor that can restrict emission to only those times in which the device output is targeted to skin, the incorporation of a sensor may prove critical to the safe use of such devices. Just as with the FDA restricted systems described above, hazards posed by inadvertent emission from these direct-sale to the consumer products include thermal damage to the eye that may cause blindness, ignition of upholstery or clothing, or in the case of devices that could treat acne with blue or near ultraviolet (U.V.) radiation, unwanted chemical damage to the eyes. Sensors that permit untrained operators to use radiation emitting devices safely on their skin may be the enabling technology for home-use self-treatment with laser and intense light dermatological devices.

However, products that are sold directly to consumers for in-home self treatment must be inexpensive, reliable, and small, and uncomplicated to use. Therefore, any diagnostic system incorporated into a device intended for the consumer market is also preferably inexpensive, reliable, and small, and simple.

It should be noted that devices that merely sense and require contact with a surface prior to emission do increase the safety of these types of systems. However, a mere contact sensor can be easily fooled by surfaces other than skin. Therefore, a system that uses a sensor that can discriminate between skin and other surfaces in conjunction with a contact sensor, would be much more reliable in detecting surfaces that are not skin.

Current State of the Art

The current state of the art of light-based dermatological devices is well described by considering typical devices available on the market. Two devices for light-based epilation are the LightSheer diode laser system manufactured by Lumenis Ltd., and the SLP-1000 fiber-coupled diode laser by Palomar Medical Technologies, Inc. Lasers and intense pulsed light systems are also used for the treatment of benign pigmented lesions and for photo-rejuvenation. An intense pulsed light (IPL) system, the Quantum, which is a powerful flashlamp system, also manufactured by Lumenis Ltd, is commonly used for photo-rejuvenation. These systems can be characterized by their relatively high radiation output. Typically these systems deliver greater than 10 $J/cm^2$, in time periods from about 5 ms to 500 ms, with optical emission powers typically in the range from 500 W to 2000 W. These devices are generally hazardous and are not appropriate for use by untrained personnel and their sale is often restricted to physicians.

More recently, much lower power devices such as a hair removal device manufactured by Ya-Man Ltd. Of Tokyo, and lower power blue LED devices for the treatment of acne have become available but have questionable efficacy or require long treatment times for use. These devices are typically capable of no more than about 1 W of radiative emission and are much less hazardous than the equivalent physician models or pose virtually no hazard at all. While these lower power systems do not require any features or devices to ensure safe use by the consumer, the trade off is questionable efficacy.

A consumer based device that is more efficacious, however, would require higher output power levels, would be inherently hazardous, and would benefit greatly from devices that would ensure safe use. Higher power consumer models, in general, are not currently available on the market not only because of safety concerns, but also because a small, reliable, inexpensive, and self-contained device, that can be conveniently used and stored by the average consumer is not easily conceived.

It is common for systems currently marketed for professional use to have safety features that restrict the emission of the devices to only those times when certain procedures are followed or certain conditions exist. For example, the LightSheer system manufactured by Lumenis, Inc. and used for laser hair removal, requires the operator to press and hold a footswitch prior to pulling the handpiece trigger that causes laser emission. The E-2000 system manufactured by Palomar, Inc., also used for laser hair removal, has perhaps the most advanced safety system of all of these dermatological systems. The E-2000 system uses a thermistor located near the output aperture of the device to measure changes in the temperature of the output aperture that occur if the device is in contact with skin. Based on these measurements of the temperature, automatic firing is restricted to times when the device is in contact with skin. This temperature safety system is presumably described in U.S. Pat. No. 6,508,813.

Characteristics of skin other than its temperature and thermodynamic properties could be used to identify skin. For example, electrical resistivity, hardness, chemical makeup, or acoustic properties would distinguish skin from other materials. However, the inventors of the subject application have identified through experiments a property of skin believed to have characteristics that are fairly unique and easily measured—its optical properties, specifically, the amount of radiation that is remitted at various wavelengths. Optical remittance is used herein to mean the total amount of light returned by a surface whether by spectral reflection, diffuse reflection, or by surface or subsurface scattering. Therefore, the remittance of skin would depend at least upon its index of refraction, roughness, optical absorption coefficient and optical scattering coefficient. Since several components of skin (blood, water, sebum, melanin, etc.) have optical absorption coefficients and optical scattering coefficients that are wavelength dependent, one would expect that the fraction of light remitted by skin would also depend on wavelength. Thus, in accordance with the present invention, the spectral remittance of skin, which is to mean the optical remittance as a function of wavelength, can be used to discriminate skin from other materials.

The spectral remittance of skin has been known and studied for years. In scientific papers as long ago as 1929, Bursting et al. described using a spectrophotometer to measure the optical remittance of skin as a function of wavelength. (See, Bursting, L. A. et al., "The Color of the Skin as Analyzed by Spectrophotometric Methods: II. The Role of Pigmentation", The Journal of Clinical Investigation, 1929, vol. 7, pp 574-592; and Bursting, L. A. et al., "The Color of the Skin as Analyzed by Spectrophotometric Methods: III. The Role of Superficial Blood", The Journal of Clinical Investigation, 1929, vol. 7, pp 593-613.) These papers identified the role of pigmentation and blood. Interestingly, a plot of spectral remittance versus wavelength shows characteristic dips at about 400 nm and 570 nm due to blood, and addition dips at about 740 nm and 980 nm due to water (see for example, U.S. Pat. No. 4,423,736). Overall remittance increases with wavelength through the visible portion of the electromagnetic spectrum due to decreasing absorption of melanin. Research shows that the characteristic spectral remission of skin is largely population-independent. Thus, it is conceivable to create a skin detector that could work reliably for skin from persons with different skin color due to different ethnicities.

Much of the recent research on the spectral remittance of skin has been done with the goal of discriminating diseased tissue from unaffected tissue. Since the optical properties of diseased and non-diseased skin can be expected to be much more subtle than the differences between the optical properties of skin and other materials such as plastic, textiles, or air, the light sources and detection systems used for these apparatuses are big, complex, and expensive.

In U.S. Pat. No. 4,423,736, DeWitt, et al. describe a system that uses a broad-band light source, filters, bifurcated optical fibers and a computer controlled spectroradiometer to measure the spectral remittance of skin for the identification of erythema. In addition to being large, complicated and expensive, the method involves obtaining a "baseline" spectral remittance from the individual's skin that is being analyzed. Obtaining a personalized baseline for each user of a dermatological device is unpractical. The light source and spectroradiometer are bulky and unsuitable for use within a small inexpensive dermatological treatment device.

In U.S. Pat. No. 4,486,184, Comment, et al. describe a device to measure the diffuse reflection and specular reflection of skin. Specular reflection, meaning a reflection whose incident angle is equal to its angle of reflection, should not be confused with spectral reflectivity, meaning the wavelength dependent reflectivity of a material. Although the device that is described has a means for radiating the skin and detecting the reflectance, and it is believed that there is no disclosure of a means for measuring the reflectance as a function of wavelength. Measuring the spectral reflectance of skin is more involved and is typically performed using large spectrophotometers.

In U.S. Pat. No. 5,556,612 Anderson et al. describe a method for treating diseased skin, especially skin affected by psoriasis. The method includes a step in which a non-invasive optical diagnostic method involving measuring the reflectance properties of diseased skin is used to determine the amount of topical photo-protection to apply to skin prior to radiation therapy. The non-invasive optical diagnostic is described as a measurement of the diffuse reflectance of light from the skin at the wavelength of the radiation used for treatment. It is believed that method and the device described do not measure the spectral reflectance of the skin, are not used to differentiate skin from other materials and it is not used to inhibit the delivery of therapeutic radiation.

In U.S. Pat. No. 5,628,744, Coleman, et al. describe a dermatological treatment device that incorporates two beams of radiation—a probe beam and a treatment beam. The reflectance of the probe beam is used to discriminate diseased skin form non-diseased skin. The probe beam, however, is described as monochromatic. Measuring the spectral reflectance of skin is more involved and is typically performed using large spectrophotometers.

Again, in U.S. Pat. No. 6,208,749, Gutkowicz-Krusin et al. describe a method and device for discriminating diseased tissue from normal tissue. Although the spectral remittance of the skin is measured, the method and device rely on the imaging of the skin and rely on an algorithm that demarks the boundary between diseased and normal tissue. The detector (imager), and a processor capable of manipulating the image data are relatively complex and not appropriate for use within a handpiece of a dermatological treatment device.

Lastly, in U.S. Pat. No. 6,436,127, Anderson, et al. describe a method for discriminating diseased skin that uses two different optical diagnostics. However, a method or device suitable for discriminating skin from other materials that requires only one optical diagnostic that is simple, small, inexpensive, and reliable is not described.

In summary, the current state of the art for home-use radiative therapeutics is limited to lower power devices of questionable efficacy. Safety features are not a concern in current home-use treatment devices because of their low output levels. Safety features in higher-power treatment devices for use by physicians are basic or not present because of the assumption that use is limited to trained, skilled operators. The radiative diagnostics that do exist in current therapeutic devices rely on simple techniques that require less complicated devices, or rely on methods that do not perform multi-wavelength measurements. Otherwise, the current state diagnostics rely on more complicated, and expensive techniques that involve the use of large, expensive, and complex spectroradiometers and spectrophotometers not well suited for use in a device intended for use by untrained and unskilled persons for self-treatment.

Clearly, a small, simple, inexpensive, and reliable sensor capable of discriminating skin from other materials for use as a safety feature of a dermatological treatment device would be desirable and beneficial. Furthermore, a dermatological treatment device that is powerful enough to provide efficacious treatment, has the convenience of a device small enough to fit entirely within the hand of the user, and incorporates appropriate sensors to ensure safe use by untrained, unskilled persons for self-treatment, would be desirable.

SUMMARY OF THE INVENTION

In accordance with a first aspect of the present invention, a device and method are provided for sensing the presence of human skin by evaluating the spectral remittance of electromagnetic radiation from the surface in question. In a simple form, the apparatus uses three or more LED's, each emitting radiation at a unique wavelength. Each LED, in turn, is used to illuminate the surface in question and the remitted light is measured by a detector, such as a silicon photo transistor. The remitted intensity at each wavelength is then compared with the known spectral remittance that is characteristic of skin. This configuration is described in more detail in the detailed description section of the subject application.

In accordance with the present invention, many other configurations of the sensor are also contemplated. For example, a single light source that emits at more than one wavelength such as an incandescent bulb could be used in combination with multiple detectors, each detector being capable of measuring the intensity of the remitted light within a narrow spectral band. Yet another configuration would use a single, broad band emitter such as an incandescent bulb, and single, broad band detector such as a silicon photo detector, and an optical filter wheel positioned in front of either the source or detector. The filter wheel would contain three or more filters; each filter passing a different portion of the electromagnetic spectrum. In turn, each filter would be rotated into the optics path and the remittance for each wavelength measured.

Furthermore, in another embodiment of the present invention, a dermatological treatment device incorporates a skin sensor that controls emissions from the treatment device. A preferred embodiment of such a device is battery powered, self-contained, and cordless. Such a device can incorporate one or more laser diode bars, for the treatment of unwanted hair. Another variation of such a device uses one or more blue LED's to emit an intense blue light for the treatment of acne. Each of the devices ensures safe use by inhibiting the emission of radiation unless skin is detected at the output aperture of the device. The device may also include a contact sensor that prevents emission of radiation unless there is also contact between the output aperture and a sufficiently firm surface such as skin.

It is therefore an object of the present invention to provide a method and apparatus for sensing the presence of human skin by evaluating remitted radiation from a surface in question against a known spectral remittance that is characteristic of skin.

It is another object of the present invention to provide a small, simple, inexpensive, and reliable sensor capable of discriminating skin from other materials for use as a safety feature in dermatological treatment devices.

It is a further object of the present invention to provide dermatological devices which are powerful enough to provide efficacious treatment, yet small enough to fit entirely within the hand of a user, and which incorporate a skin sensor to permit safe use by untrained, unskilled persons in a self-treatment environment.

It is still another object of the present invention to provide a skin sensor which employs a light source that provides light in three or more wavelength bands onto a surface being queried, a detector responsive to light remitted in the three or more wavelength bands from the surface being queried, and a circuit coupled to the detector which measures a spectral remittance of the surface being queried, and compares the spectral remittance against a reference spectral remittance for skin.

It is a still further object of the present invention to provide a dermatological treatment device which is self-contained, hand-held, and battery powered, and which has a skin sensor that inhibits the emission of treatment radiation from the treatment device unless the presence of skin is detected.

These and other objectives, features, and advantages of the present invention will become more readily apparent upon consideration of the following detailed description of certain preferred embodiments of the present invention and accompanying drawings.

INCORPORATION BY REFERENCE

What follows is a list of citations corresponding to references which are, in addition to those references cited above and below, and including that which is described as background and the invention summary, hereby incorporated by reference into the detailed description of the preferred embodiments below, as disclosing alternative embodiments of elements or features of the preferred embodiments that may not otherwise be set forth in detail below. A single one or a combination of two or more of these references may be consulted to obtain a variation of the elements or features of preferred embodiments described in the detailed description below. Further patent, patent application and non-patent references are cited in the written description and are also incorporated by reference into the preferred embodiment with the same effect as just described with respect to the following references:

U.S. Pat. Nos. 4,423,736; 4,846,184; 5,556,612; 5,628,744; 5; 6,208,749; 6,436,127; 6,508,813; and United States published application No. 2003/0036751; and U.S. provisional patent application No. 60/451,091, filed Feb. 28, 2003; 60/456,379, filed Mar. 20, 2003; 60/458,861, filed Mar. 27, 2003; 60/472,056, filed May 20, 2003; 60/450,243, filed Feb. 25, 2003; 60/450,598, filed Feb. 26, 2003; 60/452,304, filed Mar. 4, 2003; 60/451,981, filed Mar. 4, 2003; 60/452,591, filed Mar. 6, 2003; and 60/456,586, filed Mar. 21, 2003, all of which are assigned to the assignee of the subject application;

U.S. non-provisional patent application Ser. No. 10/783,880, filed Feb. 19, 2004, now U.S. Pat. No. 7,250,045, entitled "Self-Contained Eye-Safe Hair-Regrowth-Inhibition Apparatus And Method," naming as inventors Tobin C. Island, Robert E. Grove, and Mark V. Weckwerth; Ser. No. 10/783, 603, filed Feb. 19, 2004, entitled "Eye-Safe Dermatologic Treatment Apparatus And Method," naming inventors: Robert F. Grove, Mark V. Weckwerth, Tobin C. Island; and Ser. No. 10/783,607, filed Feb. 19, 2004, now U.S. Pat. No. 7,118,563, entitled "Self-Contained, Diode-Laser-Based Dermatologic Treatment Apparatus And Method," naming as inventors: Mark V. Weckwerth, Tobin C. Island, Robert F. Grove, all of which are assigned to the assignee of the subject application (collectively "the Cross-Referenced Non-Provisional Applications").

Angelopoulou et al., "The Reflectance Spectrum of Human Skin", Technical Report, Department of Computer and Information Science, 1999;

Bursting, L. A. et al., "The Color of the Skin as Analyzed by Spectrophotometric Methods: II. The Role of Pigmentation", The Journal of Clinical Investigation, 1929, vol. 7, pp 574-592; and Bursting, L. A. et al., "The Color of the Skin as Analyzed by Spectrophotometric Methods: III. The Role of Superficial Blood", The Journal of Clinical Investigation, 1929, vol. 7, pp 593-613.

DETAILED DESCRIPTION OF THE PREFERRED EMBODIMENTS

Figure 1:
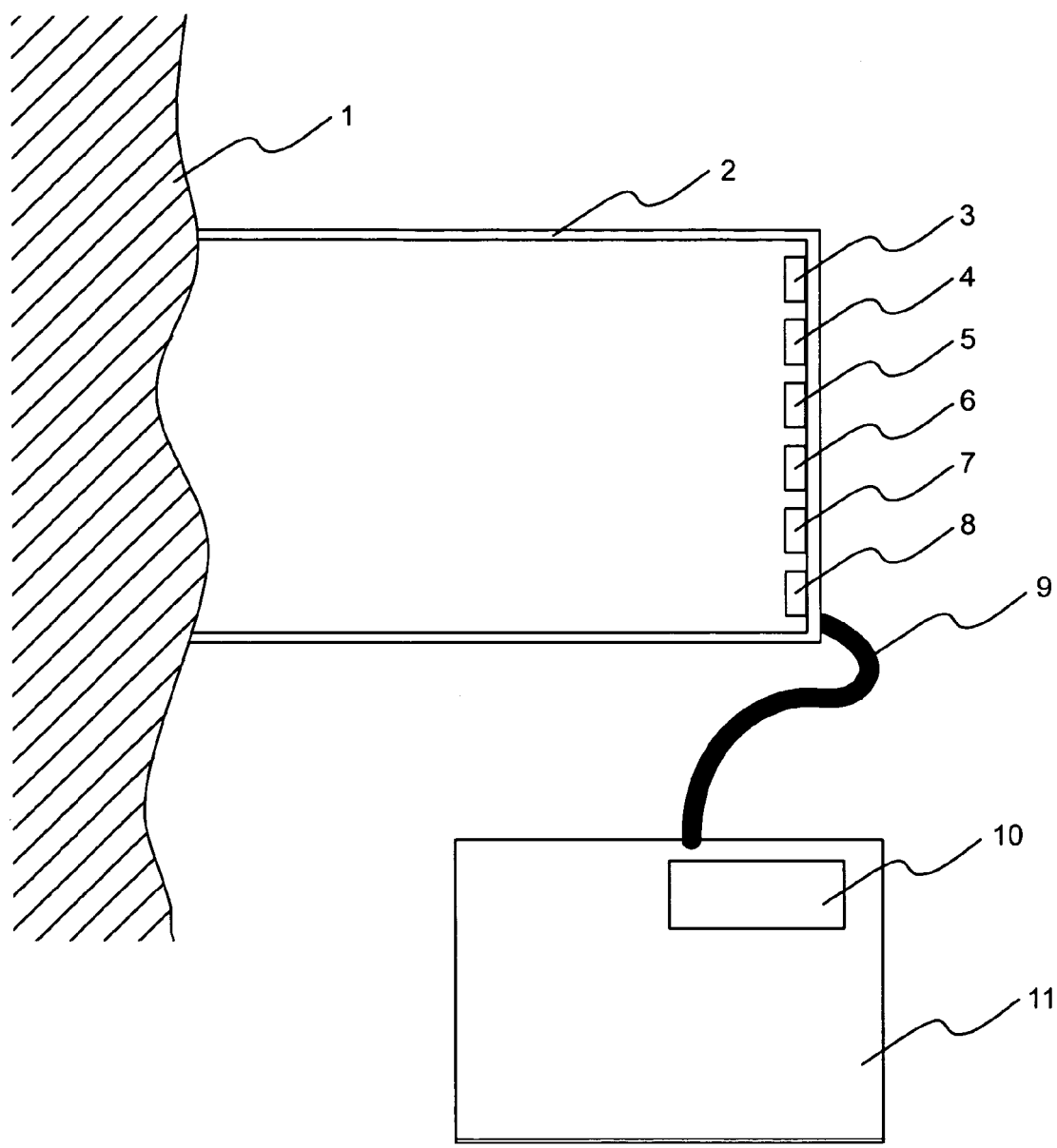
FIG. 1 is a simplified illustration of a sensor in accordance with the present invention.
Figure 2:
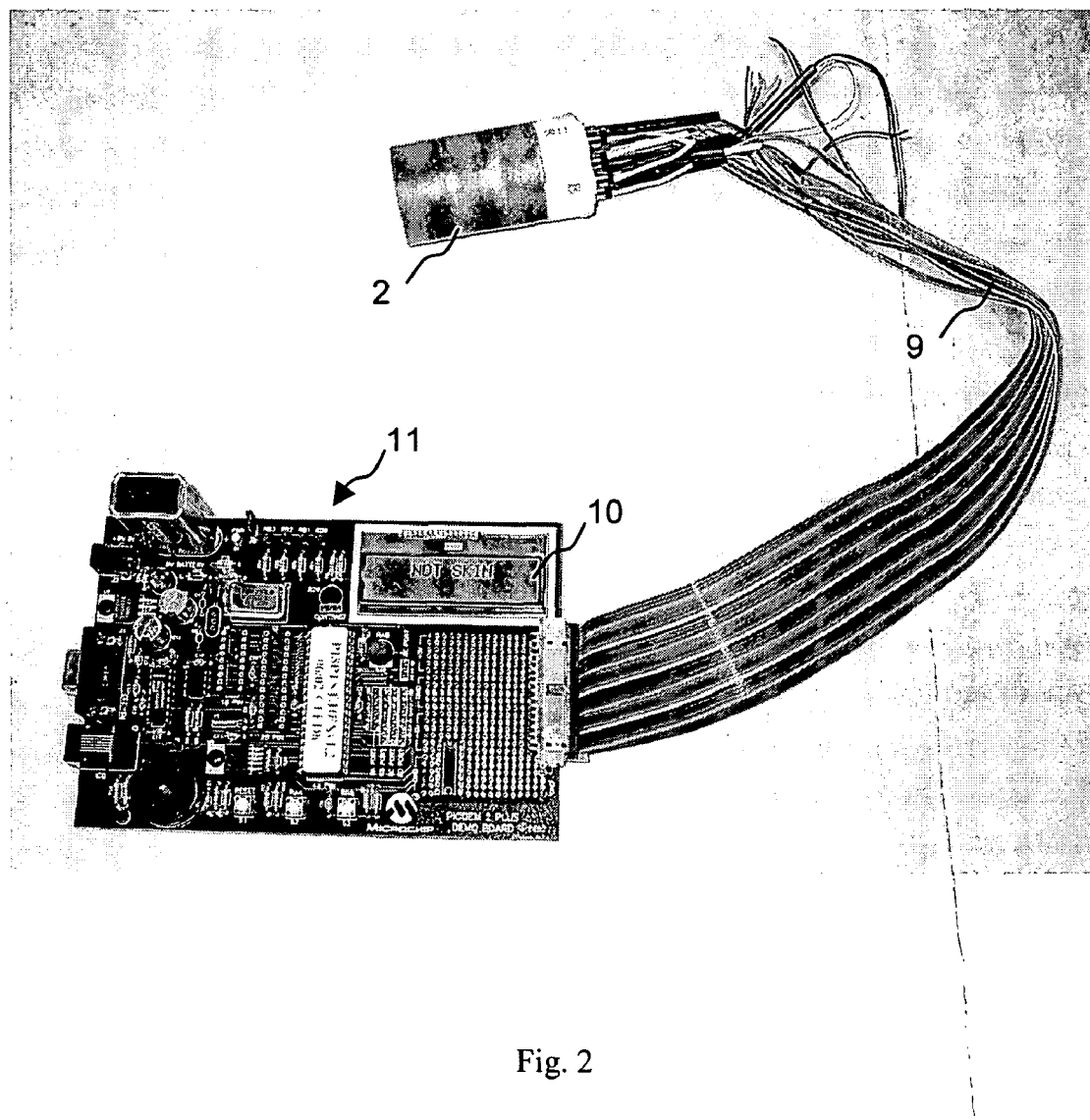
FIG. 2 is a photograph of a sensor including control circuitry in accordance with one embodiment of the present invention.

A detailed description of a configuration of the invention that uses multiple LED's as a light source and a single detector will now be described. FIG. 1 shows a drawing of such a sensor. While five (5) LED's are shown in FIG. 1, a smaller or greater number of LED's or other light sources can be used in this embodiment within the spirit of the present invention. FIG. 2 shows a photograph of the sensor, including control electronics.

The sensor of this embodiment has a chamber 2 that contains light sources 3, 4, 6, 7, and 8 and detector 5. Chamber 2 is open on the end opposite to the light sources 3, 4, 6, 7, and 8 and detector 5. Chamber 2 is made of an optically opaque material to prevent saturation of detector 5 by ambient lighting. In another embodiment of the current invention, light sources 3, 4, 6, 7, and 8 could be modulated so that frequency detection techniques can be used to resolve a relatively small signal from detector 5 even in the presence of strong ambient lighting. In such an embodiment, chamber 2 would not need to be opaque or chamber 2 could be eliminated.

Figure 3:
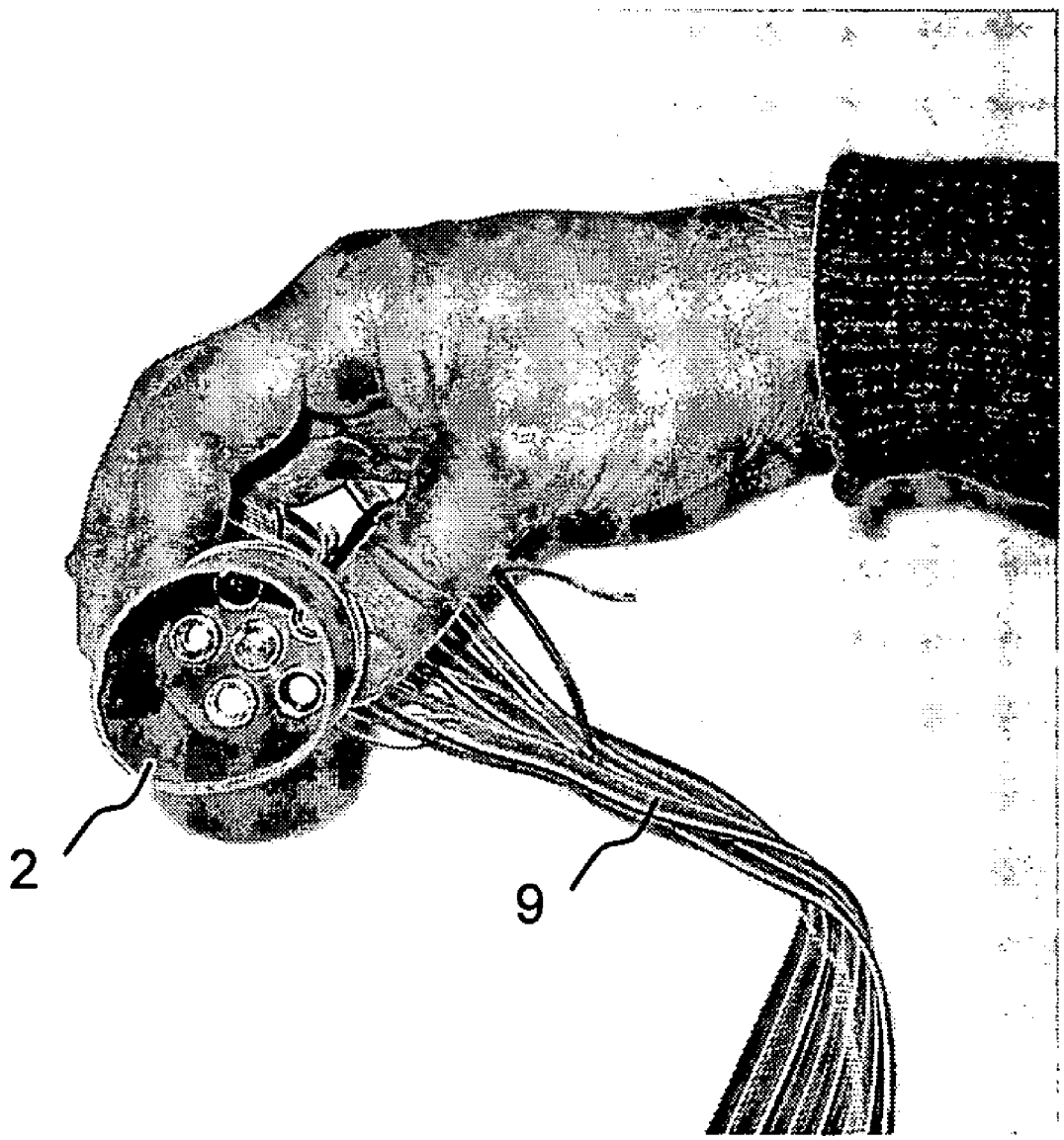
FIG. 3 is a photograph of the sensor of FIG. 2, looking into the chamber.

As shown in FIG. 2, the chamber can be made of a 1.5 inch diameter cardboard tube 2.75 inches in length. The closed end of the chamber is made by securing, such as by taping, an opaque disk of blue plastic over the end of the tube. A photograph looking into chamber 2 is shown in FIG. 3.

Light sources 3, 4, 6, 7, and 8 and detector 5 are mounted into holes drilled through the blue plastic disk. Light source 3 can be an infra-red LED with a typical peak emission at 940 nm (Radio Shack of Fort Worth, Tex., part # 276-143). Light source 4 can be a red LED with a typical peak emission at 660 nm (Radio Shack part # 276-309). Light source 6 can be a yellow LED with a typical peak emission at 587 nm (Radio Shack part # 276-351). Light source 7 can be a green LED with a typical peak emission at 565 nm (Radio Shack part # 276-304). Light source 8 can be a blue LED with a typical peak emission at 468 nm (Radio Shack part # 276 -316). Detector 5 can be a silicon npn photo transistor (Radio Shack part # 276-145). Alternatively, the light source and detector could be located remotely to the chamber and the light could be transported to and from the chamber through fiber optics or light pipes.

Figure 4:
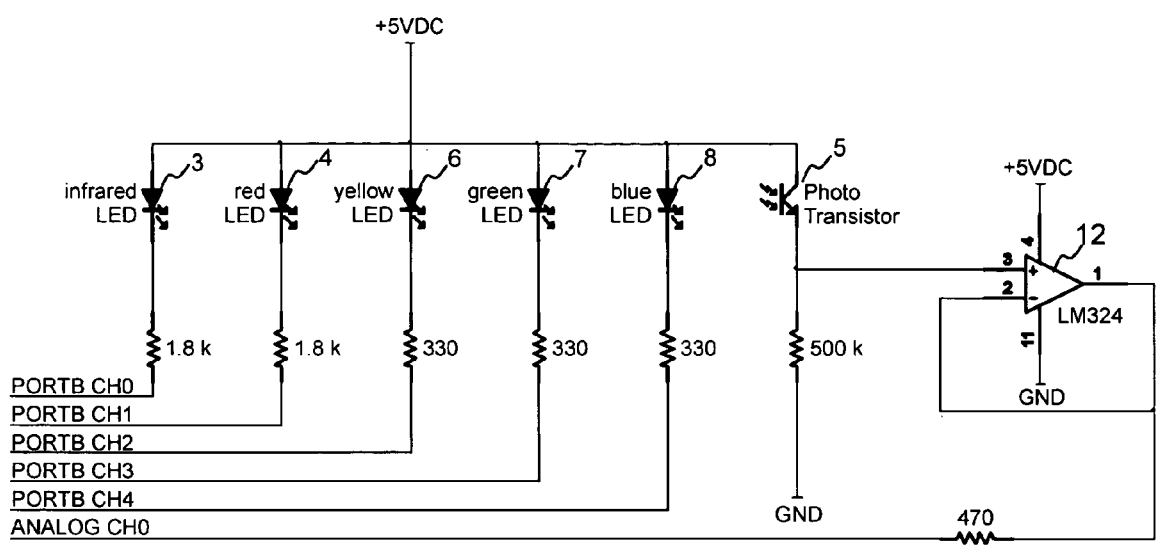
FIG. 4 is a simplified schematic diagram of a configuration of light sources and detector in accordance with an embodiment of the present invention.

Cable 9 is used to connect chamber 2, light sources 3, 4, 6, 7, and 8, and detector 5 to a microprocessor board 11. In the embodiment shown in FIGS. 3 and 4, microprocessor board 11 is a PICDEM 2 Plus Demo Board manufactured by Microchip, Inc. of Chandler, Ariz. The board was modified so that output pins on PORTB of the processor could turn on each light source 3, 4, 6, 7, and 8 individually. The board was also modified so that the output signal from detector 5 could be read by the analog input channel 0 of the processor. The board has a display 10 on which an indication of "SKIN" or "NOT SKIN" is made. Also included is an amplifier which is connected to receive the output of the detector 5, and to drive the analog input channel 0. The amplifier can be a LM324 operational amplifier, manufactured by National Semiconductor of Sunnyvale, Calif., connected as a voltage follower. A diagram of the electrical connections of the light sources 3, 4, 6, 7 and 8, the detector 5, the amplifier 12, and signal pins of the processor is given in FIG. 4.

In normal use, the open end of chamber 2 is placed against the surface to be measured, surface 1. The processor first measures the signal from detector 5 with all of the light sources 3, 4, 6, 7, and 8 off. This is the dark value and is used as a base-line for the signals of subsequent measurements. In turn, the processor turns on each of the light sources 3, 4, 5, 7, and 8, one-at-a-time, and measures the signal from detector 5 to arrive at an infra-red value, a red value, a yellow value, a green value, and blue value respectively. The measured dark value is subtracted from each of the measured radiation values to generate a set of adjusted values. "SKIN" is displayed on the display, indicating the presence of skin, if the following conditions are met for these adjusted values:

(infra-red value−dark value)>30

(infra-red value−dark value)<50

(green value−dark value)<10

(yellow value−dark value)<25

(red value−dark value)>40

Otherwise, "NOT SKIN", is displayed by the processor.

One skilled in the art will appreciate that the absolute numbers provided in the foregoing example are in arbitrary units, and that it is the relative relationship between these adjusted values that is of primary significance in the skin sensing method of the present invention.

The methodology described above is quite simple yet has proved to be very reliable in distinguishing human skin from a broad range of other surfaces such as cloth, metal, plastic, wood, etc. in experiments run by the inventors herein. Typical values obtained for various materials are given in Table 1. It has been found that a criterion for the remittance in the blue wavelength band was not needed to distinguish skin from common materials found in the office or home. Criteria for the blue remittance or a more complicated set of conditions for all of the color values can be developed that would provide even better discrimination between skin and other materials. However, a set of criteria that is too restrictive may not identify correctly some skin types since there is some variability in the optical properties of human skin. Conversely, if a lesser degree of discrimination is required for a certain application, then fewer light sources or a less restrictive set of criteria could be used. For any application, the complexity of the source and detector, the degree of discrimination desired, and tolerance of false negatives should be considered in determining the optimal design.

TABLE 1

|  | Caucasian skin | Asian skin | dark room | white paper | blue shirt | green paper | red plastic | wood | leather |
|---|---|---|---|---|---|---|---|---|---|
| dark | 0 | 2 | 1 | 0 | 0 | 0 | 0 | 0 | 0 |
| infrared | 40 | 43 | 7 | 91 | 67 | 82 | 84 | 44 | 66 |
| red | 57 | 61 | 6 | 101 | 18 | 24 | 103 | 27 | 41 |
| yellow | 14 | 20 | 2 | 46 | 7 | 12 | 22 | 17 | 16 |
| green | 4 | 7 | 2 | 15 | 2 | 4 | 5 | 5 | 4 |
| blue | 13 | 19 | 3 | 60 | 17 | 15 | 8 | 16 | 9 |

The device just described could be miniaturized through the use of surface mountable LED's and detectors commonly found in packages as small as 0.06"×0.03" (SMT 0603 packages). The entire detector optical assembly could then be as small as 1 cm$^3$ or smaller. Through the use of surface mountable microcontrollers, resistors, and LED indicators, the electronics could be miniaturized to an equally small volume. Thus the device could be suitable for use as part of a small battery powered dermatological device.

Further, it is to be understood that in a commercial product, the devices, circuits and structures shown in FIGS. 1 through 4 can be incorporated into a more compact and integrated configuration, typically as a part of a treatment or therapeutic device. One such suitable configuration is described in the aforementioned Cross-Referenced Non-Provisional Applications, for example in US Non-Provisional Patent Application, entitled "Self-Contained Eye-Safe Hair-Regrowth-Inhibition Apparatus And Method," incorporated by reference herein. In this cross-referenced application a self-contained, cordless, battery powered device is described. The device includes a housing which accommodates light sources, batteries, and electrical circuitry. In particular, FIG. 11 of the cross referenced application is a block diagram of the electronic circuitry for such device which can accommodate the specific light sources, amplifiers, and processing operations described herein. For example, in FIG. 11 of the cross-referenced application there is a skin sensor block 890 which communicates with a processor block 888 and with LED's 853, 854 and detectors 855, 856. One skilled in the art will readily appreciate that the processor block 888 can provide the processing operations performed by the processor of microprocessor board 11 described herein; and that skin sensor block 890 and LED's 853, 854 and detectors 855, 856 can correspond to the light sources 3, 4, 6, 7, and 8, and the detector 5, described herein.

In another embodiment of the sensor of the current invention a single broad-band radiation source such as an incandescent bulb is substituted for the multiple LED's. This embodiment employs multiple detectors, each sensitive to a distinct wavelength band. The control circuit measures the signal from each of the detectors. The detectors can be made sensitive to unique wavelength bands through the use of optical filters or by using detectors composed of materials inherently sensitive to different wavelength bands such as are gallium arsenide (GaAs), silicon (Si), and gallium nitride (GaN).

A Safe Therapeutic Dermatological Device Embodiment

Figure 5:
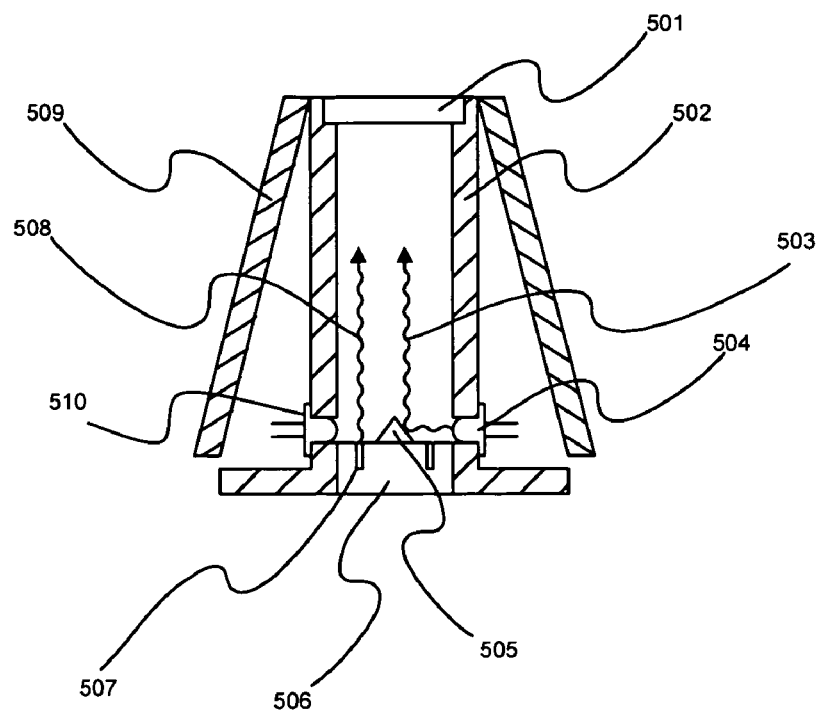
FIG. 5 illustrates the integration of an embodiment of a skin sensor into a therapeutic dermatological device in accordance with the present invention.

A drawing showing one configuration of the integration of the skin sensor into a therapeutic dermatological device is provided in FIG. 5. For clarity, only the head region near the output aperture is shown. As used in this example, the output aperture refers to the opening at the end of chamber 502 opposite radiation sources 507. Contained within housing 509 are two therapeutic radiation sources 507. A radiation source mount 506 is also shown. Radiation sources 507 may be laser diode bars that emit radiation suitable for the desired dermatological treatment. Radiation 508 is emitted from radiation source 507 into chamber 502 in the general direction of an output window 501 which is positioned in the output aperture. The skin sensor is comprised of one or more emitters 504 and one or more detectors 510 in accordance with the description of the skin sensor given previously. The emitter(s) 504 and detectors 510 can be oriented radially with respect to the light path in chamber 502. Emitted radiation 503 from the skin sensor emitters 504 takes generally a path as shown in the drawing. The emitted radiation 503 can be directed towards the same output aperture as is the therapeutic radiation 508 by a mirror 505. Thus, in the dermatologic treatment head embodiment of FIG. 5, the therapeutic radiation source 507 and the skin sensor emitters 504 and detector 510 share the same chamber 502 and the same output aperture. It is to be understood that the relative positions shown for emitter 504 and detector 510 in FIG. 5 are for illustration only, and that in practice other relative positions can be used. Also, not shown in FIG. 5 are other emitters 504 or detectors 510 positioned about the chamber 502. Further details about radiation sources 507, source mount 506, chamber 502, and output aperture 501, and therapeutic dermatologic devices in which they can be incorporated, can be found in the above mentioned Cross-Referenced Non-Provisional Applications.

Figure 6:
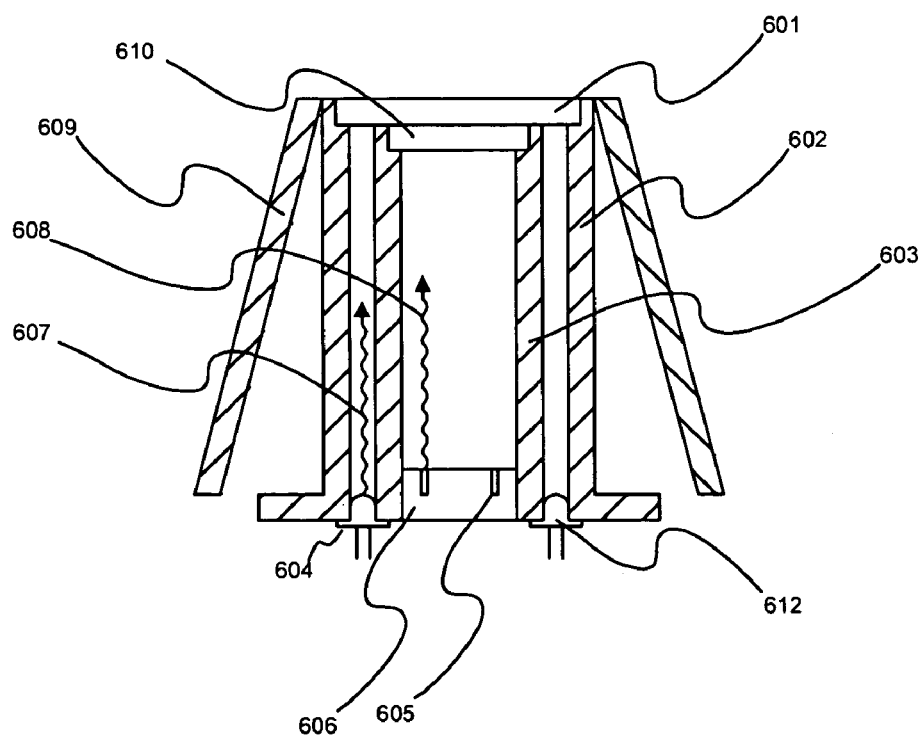
FIG. 6 illustrates an alternative integration and embodiment of the skin sensor in a therapeutic dermatological device in accordance with the present invention.

Another embodiment of a dermatological treatment head is shown in FIG. 6. This embodiment differs from the previous embodiment in that the therapeutic radiation source 605 and the skin sensor emitter 604 and detector 612 do not use the same aperture. Like the embodiment of FIG. 5, contained with housing 609 are two therapeutic radiation sources 605 mounted into source mount 606. The therapeutic radiation 608 is emitted into chamber 603 in the general direction of output window 601, and then through output window 601 which is positioned at the aperture at the end of chamber 603. In separate chamber(s) 602 along side the therapeutic treatment chamber 603 are located the emitter(s) 604 and detector(s) 612 of the skin sensor in accordance to the description of the skin sensor given previously. Emitters 604 are oriented axially with respect to a light path to the aperture. Radiation 607 from the skin sensor emitter 604 takes a path within chamber 602 as shown generally in the drawing. Thus, the skin sensor of this embodiment uses an anular-shaped aperture formed at the end of chamber 602, while the therapeutic radiation source 605 uses the aperture at the end of chamber 603. While an emitter 604 is shown on one side of the dermatological treatment head and detector 612 is shown on the other side thereof, it is to be understood that there may be other emitters 604 or detectors 612, not shown in FIG. 6, positioned adjacent to or spaced apart from the ones shown. In addition, other relative positions than the ones shown for emitter 604 and detector 612 may be used within the spirit of the present invention.

In the case of high power radiative therapeutic devices, it may be desirable to include a diffusing optical element 610 in the therapeutic beam that would reduce the eye hazard posed by the device. Diffuser 610 may also extend over the aperture of the skin sensor if desired without rendering the skin sensor inoperable. Further details about radiation sources 605, source mount 606, chamber 603, output aperture 601, diffuser 610, and therapeutic dermatologic devices in which they may be incorporated, may be found in the above mentioned Cross-Referenced Non-Provisional Applications.

Figure 7:
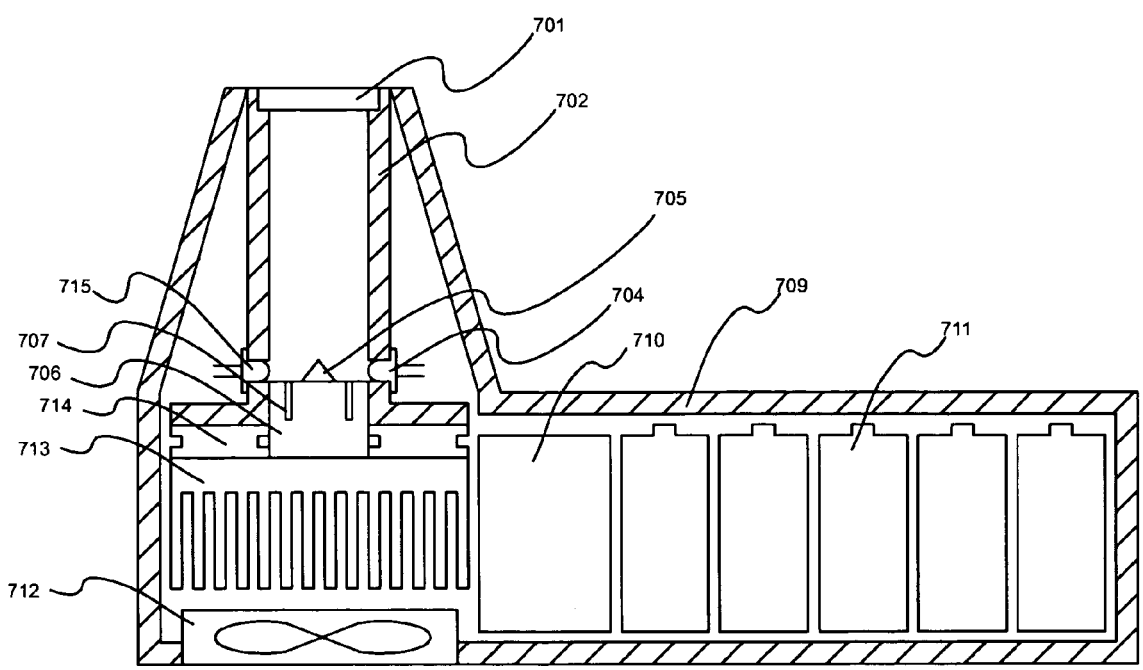
FIG. 7 illustrates a self-contained dermatological device incorporating the sensor embodiment of FIG. 5 in accordance with the present invention.

Referring now to FIG. 7, an example of a safe, small, yet powerful and efficacious dermatological device is shown which employs the therapeutic treatment head configuration of FIG. 5. Through innovative use of efficient radiation sources such as LED's or laser diodes, solid state thermoelectric coolers, innovative and efficient circuit design, and the integration of contact sensors and skin sensor, the device shown is entirely self-contained, small and light enough to fit within the grasp of a person's hand. One or more therapeutic radiation sources 707 are position within a mount 706. Therapeutic radiation source 707 is positioned such that radiation is emitted into chamber 702 and directed towards output window 701. Skin sensor radiation sources 704 and radiation detectors 715 are position to emit and collect radiation, respectively, from the aperture in housing 709. Output window 701 is kept cool by the conduction of heat through the walls of chamber 702, through thermoelectric (TE) cooling module 714, and finally into finned heat sink 713 which is cooled convectively by fan 712. Electronics 710 control emission of therapeutic radiation, the skin sensor and other devices within housing 709. Battery pack 711 provides power to the device. Reference is made to the above mentioned Cross-Referenced Non-Provisional Applications which provide further details about suitable dermatological devices of this type.

In other embodiments of the dermatological device of FIG. 7, other suitable radiation sources such as LED's or flashlamps are substituted for radiation sources 707. Also, some dermatological applications do not require the output window 701 to be thermally linked to the thermoelectric cooling modules 714. Still other embodiments of a suitable device would use a wired connection to another source of electrical power external to the handpiece portion of housing 709. In other embodiments, the finned heat exchanger 713 may be replaced by a thermal battery or other type of heat exchanger that may incorporate the use of water.

More specifically, the preferred embodiment of a laser hair removal device would be a self-contained, cordless device. It would use one or more laser diode bars to produce emission at about 808 nm. The exposure times of the skin would be about 400 ms, with the fluence of the exposure about 20 J/cm$^2$. The optical output power of the device preferably would be 60 W with a preferable treatment area of about 1 cm$^2$. The weight of the device would be about 750 g and the volume would be about 1000 cm$^3$. The safety features of the device would include a contact sensor and skin sensor. The device may also be made inherently less hazardous to a users' eyes through the use of a diffuser within the device that reduced the integrated radiance of the emission. Suitable diffusers are described in the Cross-Referenced Non-Provisional Applications.

A preferred embodiment of an acne treatment device in accordance with the present invention would be a self-contained, cordless device. It would use one or more LED's to produce emission at about 412 nm. The exposure times of the skin would be about 10 s, with the fluence of the exposure about 25 J/cm$^2$. The optical output power of the device would be about 2.5 W with a treatment area of about 1 cm$^2$. The weight of the device would be about 500 g and the volume would be about 500 cm$^3$. The safety features of the device would include a contact sensor and skin senor. The device may also be made inherently less hazardous to the users' eyes through the use of a diffuser with the device that reduced the integrated radiance of the emission.

A preferred embodiment of a repigmentation device in accordance with the present invention would be a self contained, cordless device. It would use one or more LED's to produce emission in the wavelength range from 320 nm to 399 nm. The optimal power, and duration of the emission would depend strongly on the wavelength because of the higher effectiveness of shorter wavelengths. However, for a device producing radiation at 370 nm, 240 mW through an aperture 3 mm in diameter would generate about 33 J/cm$^2$ in about ten seconds. This dose would provide a significant fraction of a minimum erythemic dose (MED). The weight of the device would be about 500 g and the volume would be about 500 cm$^3$. The safety features of the device would include a contact sensor and skin senor. The device may also be made inherently less hazardous to the users' eyes through the use of a diffuser within the device that reduced the integrated radiance of the emission.

While exemplary drawings and specific embodiments of the present invention have been described and illustrated, it is to be understood that that the scope of the present invention is not to be limited to the particular embodiments discussed. Thus, the embodiments shall be regarded as illustrative rather than restrictive, and it should be understood that variations may be made in those embodiments by workers skilled in the arts without departing from the scope of the present invention, as set forth in the appended claims and structural and functional equivalents thereof.

In addition, in methods that may be performed according to preferred embodiments herein and that may have been described above, the operations have been described in selected typographical sequences. However, the sequences have been selected and so ordered for typographical convenience and are not intended to imply any particular order for performing the operations, unless expressly set forth in the claims or as understood by those skilled in the art as being necessary.

What is claimed:

1. A skin sensor comprising, a housing having an aperture shaped to be placed against a surface being sensed; a radiation source inside said housing and positioned to emit radiation in three or more distinct wavelength bands through said aperture and onto said surface being sensed so that radiation is remitted by the surface being sensed; a detector inside said housing positioned to receive the radiation remitted by said surface being sensed; a control circuit to power said radiation source so that radiation from each of the three or more distinct wavelength bands is emitted at distinct times; said control circuit further measuring the remitted radiation for each said three or more distinct wavelength bands to obtain a spectral remittance of said surface being sensed; said control circuit further comparing the spectral remittance of the surface being sensed to a reference spectral remittance previously determined for skin; said control circuit providing an indication when the spectral remittance of the surface being sensed is substantially the same as the reference spectral remittance.

2. The skin sensor of claim 1, wherein the radiation source comprises a plurality of light emitting diodes, each emitting radiation in a different one of the three or more distinct wavelength bands.

3. The skin sensor of claim 2, wherein the radiation source includes light emitting diodes each of which emit radiation in a different one of an infra-red, a red, a yellow, a green, or a blue wavelength band.

4. The skin sensor of claim 2, wherein the housing is opaque.

5. The skin sensor of claim 2, wherein the radiation source is controlled to emit modulated radiation in three or more distinct wavelength bands.

6. The skin sensor of claim 1, wherein the detector comprises a plurality of radiation detectors, each responsive to radiation in a different one of the three or more distinct wavelength bands.

7. The skin sensor of claim 1, wherein the detector comprises a single broadband radiation detector.

8. A skin sensor comprising, a housing having an aperture configured to be placed against a surface being queried; a broad-band radiation source contained within said housing and positioned to emit radiation through said aperture; three or more detectors inside said housing, each responsive to a distinct wavelength band and positioned to receive radiation remitted by said surface being queried; a control circuit to power said radiation source; said control circuit further measuring the remitted radiation for each said distinct wavelength band to determine a spectral remittance of said surface being queried; said control circuit further comparing the spectral remittance of said surface being queried to a reference spectral remittance for skin; and said control circuit providing an indication when the spectral remittance of said surface being queried is substantially the same as the reference spectral remittance.

9. The skin sensor of claim 8, wherein each of the three or more detectors is composed of a material inherently sensitive to radiation in a different one of the distinct wavelength bands.

10. The skin sensor of claim 8, wherein each of the three or more detectors comprises a broadband radiation detector and a filter which passes radiation from different ones of the distinct wavelength bands.

11. A dermatological treatment device comprising, a housing having a treatment aperture configured to be placed against a surface; a source of therapeutic radiation contained within said housing and positioned to emit therapeutic radiation through said aperture; a skin sensor including a source inside said housing and positioned to emit sensing radiation in three or more distinct wavelength bands through a sensor aperture and onto said surface so that sensing radiation is remitted by the surface; a detector inside said housing positioned to receive the sensing radiation remitted by said surface; a control circuit to power said source so that the sensing radiation from each of the three or more distinct wavelength bands is emitted at distinct times; said control circuit further measuring the remitted sensing radiation for each said three or more distinct wavelength bands to obtain a spectral remittance of said surface; said control circuit further comparing the spectral remittance of the surface to a reference spectral remittance previously determined for skin; and said control circuit providing an indication when the spectral remittance of the surface is substantially the same as the reference spectral remittance.

12. The dermatological treatment device of claim 11, wherein the treatment aperture is the same as the sensor aperture; and emission of said therapeutic radiation by said dermatological treatment device is inhibited if said skin sensor indicates the absence of skin.

13. The dermatological treatment device of claim 12, further comprising a contact sensor which senses a substantial contact between said treatment aperture and said surface; and wherein emission of said therapeutic radiation is inhibited if said substantial contact is not detected.

14. The dermatological treatment device of claim 11, wherein said treatment aperture and said sensor aperture are distinct from one another, but are located sufficiently close to each other such that whenever said sensor aperture is positioned against a skin surface the entire said treatment aperture is substantially positioned against said skin surface; and emission of said therapeutic radiation by said dermatological treatment device is inhibited if said skin sensor indicates the absence of skin.

15. The dermatological treatment device of claim 14, further comprising a contact sensor which senses a substantial contact between said treatment aperture and said surface; and wherein emission of said therapeutic radiation is inhibited if said substantial contact is not detected.

16. A dermatological treatment device comprising, a housing having a treatment aperture configured to be placed against a surface; a source of therapeutic radiation contained within said housing and positioned to emit therapeutic radiation through said treatment aperture; a broad-band radiation source contained within said housing and positioned to emit sensing radiation through a sensor aperture and onto said surface; three or more detectors inside said housing, each responsive to a distinct wavelength band and positioned to receive sensing radiation remitted by said surface; a control circuit to power said radiation source; said control circuit further measuring the remitted sensing radiation for each said distinct wavelength band to determine the spectral remittance of said surface; said control circuit further comparing the spectral remittance of said surface to a reference spectral remittance for skin; and said control circuit providing an indication when the spectral remittance of said surface is substantially the same as the reference spectral remittance.

17. The dermatological treatment device of claim 16, wherein the treatment aperture is the same as the sensor aperture; and emission of said therapeutic radiation by said dermatological treatment device is inhibited if said skin sensor indicates the absence of skin.

18. The dermatological treatment device of claim 17, further comprising a contact sensor which senses a substantial contact between said treatment aperture and said surface; and wherein emission of said therapeutic radiation is inhibited if said substantial contact is not detected.

19. The dermatological treatment device of claim 16, wherein said treatment aperture and said sensor aperture are distinct from one another, but are located sufficiently close to each other such that whenever said sensor aperture is positioned against a skin surface substantially the entire said treatment aperture is positioned against said skin surface; and emission of said therapeutic radiation by said dermatological treatment device is inhibited if said skin sensor indicates the absence of skin.

20. The dermatological treatment device of claim 19 further comprising, a contact sensor which senses a substantial contact between said treatment aperture and said surface; and wherein emission of said therapeutic radiation is inhibited if said substantial contact is not detected.

21. A dermatological treatment device used for the treatment of unwanted hair comprising, a light source within a housing; an electrical circuit including one or more batteries within the housing for energizing the light source to produce output light pulses; a light path within the housing including an aperture through which eye-safe light pulses are propagated out of the housing having properties sufficient for at least temporary hair-regrowth inhibition; and a skin sensor which inhibits the operation of the light source when an absence of skin at the aperture is detected by the skin sensor; wherein the dermatological treatment apparatus has a total weight of no more than 1 kilogram, and occupies no more than 1500 cm$^3$ of volume; and whereby in use, the dermatologic treatment apparatus produces a fluence on an epidermis of a subject undergoing treatment that is sufficient to at least temporarily inhibit hair regrowth and that has an integrated radiance insufficient to cause eye damage.

22. The dermatological treatment device of claim 21, further comprising an optical diffuser disposed along the light path so that an integrated radiance of the output light pulses is reduced to an eye-safe value; and whereby in use, the dermatologic treatment has an integrated radiance insufficient to cause eye damage.

23. A dermatological treatment device used for the treatment of unwanted hair comprising, a light source within a housing; an electrical circuit including one or more batteries within the housing for energizing the light source to produce output light pulses; a light path within the housing including a treatment aperture through which eye-safe light pulses are propagated out of the housing having properties sufficient for at least temporary hair-regrowth inhibition; and a skin sensor which inhibits the operation of the light source when an absence of skin at the treatment aperture is detected by the skin sensor including a source inside said housing and positioned to emit sensing radiation in three or more distinct wavelength bands through a sensor aperture and onto a surface positioned opposite the treatment aperture so that sensing radiation is remitted by the surface; a detector inside said housing positioned to receive the sensing radiation remitted by said surface; a control circuit to power said source so that the sensing radiation from each of the three or more distinct wavelength bands is emitted at distinct times; said control circuit further measuring the remitted sensing radiation for each said three or more distinct wavelength bands to obtain a spectral remittance of said surface; said control circuit further comparing the spectral remittance of the surface to a reference spectral remittance previously determined for skin; and said control circuit inhibiting the light source when the spectral remittance of the surface is not substantially the same as the reference spectral remittance; and wherein the dermatological treatment apparatus has a total weight of no more than 1 kilogram, and occupies no more than 1500 cm$_3$ of volume; and whereby in use, the dermatologic treatment apparatus produces a fluence on an epidermis of a subject undergoing treatment that is sufficient to at least temporarily inhibit hair regrowth and that has an integrated radiance insufficient to cause eye damage.

24. The dermatological treatment device of claim 23, further comprising an optical diffuser disposed along the light path so that an integrated radiance of the output light pulses is reduced to an eye-safe value; and whereby in use, the dermatologic treatment has an integrated radiance insufficient to cause eye damage.

25. A dermatological treatment device used for the treatment of acne comprising, a skin sensor including a source inside said housing and positioned to emit sensing radiation in three or more distinct wavelength bands through a sensor aperture and onto a surface positioned opposite an output window so that sensing radiation is remitted by the surface; a detector inside said housing positioned to receive the sensing radiation remitted by said surface; a control circuit to power said source so that the sensing radiation from each of the three or more distinct wavelength bands is emitted at distinct times; said control circuit further measuring the remitted sensing radiation for each said three or more distinct wavelength bands to obtain a spectral remittance of said surface; said control circuit further comparing the spectral remittance of the surface to a reference spectral remittance previously determined for skin; and said control circuit indicating an absence of skin when the spectral remittance of the surface is not substantially the same as the reference spectral remittance; and a light source producing light primarily in a wavelength band of 400 to 450 nm and which is emitted through the output window, wherein the output window is configured to contact an epidermis of a subject undergoing treatment when the light is emitted through the output window; and wherein the light has an intensity of at least 100 mW/cm$^2$ at an emitting surface of the output window; and further wherein heat conduction through the output window is such that a temperature rise produced in the epidermis by the light is reduced by the contact between the epidermis and the output window, and light emission from the light source is inhibited when the skin sensor indicates an absence of skin at the output window.

26. A dermatological treatment device used for repigmenting skin comprising, a housing configured for handheld manipulation; one or more electrical batteries within the housing; a light source in the housing producing light primarily in a wavelength band of 320 to 399 nm; and an output window through which the light is emitted from the housing and which is configured to contact an epidermis of a subject undergoing treatment when the light is emitted through the output window, wherein the light has a spot size at the output window in the range of 0.01 to 0.5 cm$^2$; and a skin sensor coupled to inhibit the light source when the skin sensor indicates an absence of skin.

27. The dermatological treatment device of claim 26 wherein the skin sensor includes a source inside said housing and positioned to emit sensing radiation in three or more distinct wavelength bands through a sensor aperture and onto a surface positioned opposite the output window so that sensing radiation is remitted by the surface; a detector inside said housing positioned to receive the sensing radiation remitted by said surface; a control circuit to power said source so that the sensing radiation from each of the three or more distinct wavelength bands is emitted at distinct times; said control circuit further measuring the remitted sensing radiation for each said three or more distinct wavelength bands to obtain a spectral remittance of said surface; said control circuit further comparing the spectral remittance of the surface to a reference spectral remittance previously determined for skin; and said control circuit inhibiting the light source when the spectral remittance of the surface is not substantially the same as the reference spectral remittance.

28. A method for detecting the presence of skin, comprising the steps of emitting radiation onto a surface being queried; receiving radiation remitted by said surface being queried; measuring the remitted radiation in three or more distinct wavelength bands to determine a spectral remittance of said surface being queried; comparing the spectral remittance of said surface being queried to a reference spectral remittance for skin; and indicating if the spectral remittance of said surface being queried is substantially the same as the reference spectral remittance.

29. The method of claim 28, wherein the emitting step includes the step of sequentially emitting radiation in three or more distinct wavelength bands.

30. The method of claim 29, wherein the sequentially emitting step includes the steps of triggering a first radiation source to emit radiation in a first distinct wavelength band; triggering a second radiation source to emit radiation in a second distinct wavelength band; and triggering a third radiation source to emit radiation in a third distinct wavelength band.

31. The method of claim 29, wherein the sequentially emitting step includes the step of triggering a broadband radiation source to emit broadband radiation; filtering the emitted broadband radiation with a first filter to provide filtered radiation in a first distinct wavelength band; filtering the emitted broadband radiation with a second filter to provide filtered radiation in a second distinct wavelength band; and filtering the emitted broadband radiation with a third filter to provide filtered radiation in a third distinct wavelength band.

32. The method of claim 28, wherein the measuring remitted radiation step comprises the steps of measuring the remitted radiation with a plurality of radiation detectors, each sensitive to a different one of three or more distinct wavelength bands.

33. The method of claim 28, wherein the emitting step comprises the step of triggering a source of broadband radiation; and the receiving step comprises the step of receiving the remitted radiation with a broadband detector; and further including the steps of filtering the emitted broadband radiation with a first filter to produce radiation in a first distinct wavelength band; measuring the remitted radiation of the first distinct wavelength band with the broadband detector; filtering the emitted broadband radiation with a second filter to produce radiation in a second distinct wavelength band; measuring the remitted radiation of the second distinct wavelength band with the broadband detector; filtering the emitted broadband radiation with a third filter to produce radiation in a third distinct wavelength band; and measuring the remitted radiation of the first distinct wavelength band with the broadband detector.

34. A skin sensor comprising, a radiation source positioned to emit modulated radiation in three or more distinct wavelength bands through an aperture and onto a surface being sensed so that radiation is remitted by the surface being sensed; a detector positioned to receive the radiation remitted by said surface being sensed; a control circuit to power said radiation source so that modulated radiation from each of the three or more distinct wavelength bands is emitted at distinct times; said control circuit further detecting and measuring the remitted modulated radiation for each said three or more distinct wavelength bands to obtain a spectral remittance of said surface being sensed; said control circuit further comparing the spectral remittance of the surface being sensed to a reference spectral remittance previously determined for skin; said control circuit providing an indication when the spectral remittance of the surface being sensed is substantially the same as the reference spectral remittance.

\* \* \* \* \*